United States Patent [19]

King et al.

[11] 4,107,059
[45] Aug. 15, 1978

[54] POLYMER OF 1,2,4-THIADIAZOLE AND LUBRICANTS CONTAINING IT AS AN ADDITIVE

[75] Inventors: James Ping King, Lansdale; Everett A. Mailey, Norristown; Ivan Christoff Popoff, Ambler, all of Pa.

[73] Assignee: Pennwalt Corporation, Philadelphia, Pa.

[21] Appl. No.: 810,137

[22] Filed: Jun. 27, 1977

[51] Int. Cl.² .............. C10M 1/10; C10M 3/02; C08F 28/00; C08G 75/00
[52] U.S. Cl. .................. 252/28; 252/37.7; 252/41; 252/47; 528/374; 528/377
[58] Field of Search ........ 252/47.5, 47, 28, 37.2, 252/42.1, 37.7, 41; 260/79

[56] References Cited

U.S. PATENT DOCUMENTS

| | | | |
|---|---|---|---|
| 3,821,236 | 6/1974 | Ripple | 252/47 |
| 3,855,183 | 12/1974 | MacDonald | 260/79 |
| 3,904,537 | 9/1975 | Ripple | 252/47.5 |
| 3,904,619 | 9/1975 | D'Amico | 260/302 D |

*Primary Examiner*—Irving Vaughn

[57] ABSTRACT

The Polymer of 1,2,4-thiadiazole of the structure

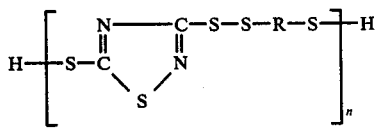

and lubricants containing said polymer are provided.

8 Claims, No Drawings

POLYMER OF 1,2,4-THIADIAZOLE AND LUBRICANTS CONTAINING IT AS AN ADDITIVE

BACKGROUND OF THE INVENTION

1. Field of Invention

This invention relates to a polymer of 1,2,4-thiadiazole that is especially effective as an additive in lubricants that enable the lubricants to withstand extremely high pressure and yet maintain antiwear properties. This invention also comprehends a lubricant composition containing such a polymer.

2. Description of the Prior Art

Polymers containing thiadiazole rings are known in the art. Minoura et al. (Chem. Abstracts, Vol. 68, 96241g, 1968), for example prepared poly(2,5-dithio-1,3,4-thiadiazole) and observed that the thermal stability of the polymer was, however, unsatisfactory. Polymers of 1,2,4-thiadiazole of this invention were not found in the prior art. However, non-polymeric disulfides of 1,2,4-thiadiazoles are known. For example, see U.S. Pat. Nos. 3,904,537, or 3,821,236 and 3,904,619. These compounds are not known to have the high-pressure, antiwear properties of the instant invention.

Many lubricants which are satisfactory for ordinary lubricating applications do not provide adequate protection under extremely heavy load conditions, such as metal deformation, cutting and grinding, gear lubrication of heavy duty machineries, and in bearing lubrication under severe conditions. Present lubricants made for these purposes include sulfurized and chlorinated hydrocarbon oils and oils containing such additives as molybdenum disulfides, tungsten sulfides, heavy metal salts of dialkyldithiocarbamic acids and dialkyldithiophosphoric acids, and organic and inorganic lead compounds.

SUMMARY OF THE INVENTION

This invention is directed to:

A. A composition having the formula:

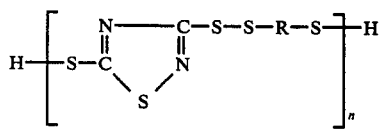

wherein:

R is selected from the group consisting of

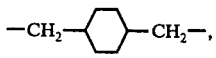,

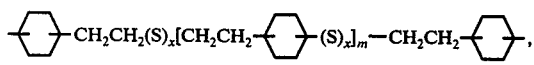,

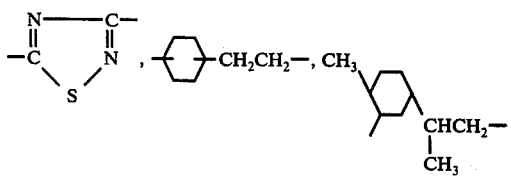

phenylene, biphenylene, an alkylene or substituted alkylene of 2-50 carbons, preferably 2-10 carbons, cyclic alkylene or substituted cyclic alkylene of 5-50 carbons, preferably 6-10 carbons, wherein the alkylene or cyclic alkylene can contain in the chain or ring oxygen and/or sulfur atoms, or $(S)_x$-groups;

$m$ is an integer of 0-10, preferably 1-5;

$n$ is an integer of 5-100, preferably 10-40; and $x$ is an integer of 1-5, preferably 1-2.

B. A lubricating composition comprising a major amount of lubricating grease (or fluid) and a minor amount of the compound described in A, supra. The major amount is 80-99.9 parts (percent) of the lubricating grease and the minor amount is 20-0.1 parts, preferably 3-5 parts, of the polymer of 1,2,4-thiadiazole.

DETAILED DESCRIPTION OF INVENTION

This invention is directed to homo- and copolymers based on 1,2,4-thiadiazole-3,5-dithiol. A dimercaptan, such as ethanedithiol, 3- or 4-(beta-mercaptoethyl)cyclohexanethiol, or 2-methyl-5-(beta-mercapto-alfa-methylethyl)cyclohexanethiol, can be used as comonomer for preparing the copolymers. The polymers of this invention are light yellow solids containing disulfide moieties and exhibit relatively good thermal stability. They can be easily suspended in the lubricant fluids.

In the definition of R of the present invention, examples of an alkylene or substituted alkylene group are

where $y$ is 1-5,

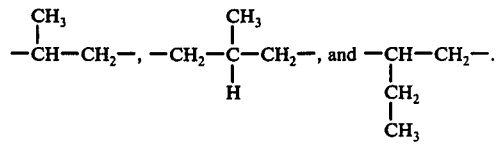

Examples of a cyclic alkylene or substituted cyclic alkylene group are

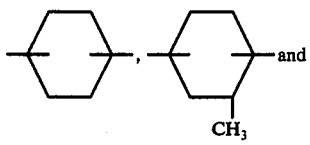

Examples of the alkylene or cyclic alkylene group containing oxygen and/or sulfur or $(S)_x$ groups are

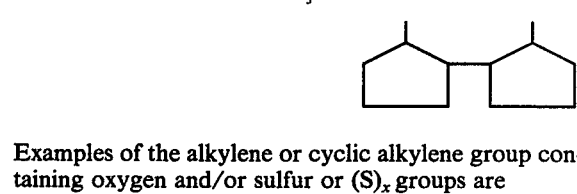

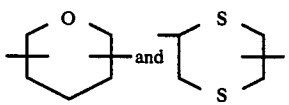

Examples of the polymer of the instant invention are: poly-(3,5-dithio-1,2,4-thiadiazole), a homopolymer of 1,2,4-thiadiazole-3,5-dithiol hereinafter called PDTD, poly-(3-[(3- or 4-thiocyclohexyl)ethyldithio]-5-thio(1,2,4-thiadiazole), a copolymer of the thiadiazoledithiol with 3- or 4-(beta-mercaptoethyl)cyclohexanethiol hereinafter called PTCETD, and poly [3-(2-thioethyldithio)-5-thio-(1,2,4-thiadiazole)], a copolymer of the thiadiazoledithiol with ethanedithiol; other examples are the copolymers of the thiadiazoledithiol with p-mercaptomethyl benzyl mercaptan, or bis (3-mercaptopropyl) ether, or mixture of 2,2'-dithiobis(3- or 4-mercaptocyclohexylethane) and dithiobis-(3- or 4-mercaptoethylcyclohexane), or a mixture of 2,2'-thiobis(3- or 4-mercaptocyclohexylethane) and thiobis(3- or 4-mercaptoethylcyclohexane).

The prior art's poly(2,5-dithio-1,3,4-thiadiazole), an isomer of poly(3,5-dithio-1,2,4-thiadiazole) (PDTD) of te present invention, was prepared and when evaluated, it was found to have a relatively low thermal stability. Its initial weight lost in air in a thermal gravimetric analysis (TGA) study occurred at about 200° C. However, an instantaneous, massive and strongly exothermic weight-loss of approximately 70 percent as opposed to 7 percent for PDTD occurred between 220° and 240° C.

This suggests that the prior art polymer based on 1,3,4-thiadiazole and PDTD of the present invention decompose by two different mechanisms; this rapid exothermic weight loss of the 1,3,4-isomer in such a narrow and relatively low temperature range will severely limit the potential use thereof as a lubricant additive. Percentages of residual weights of these two polymers in a temperature range of 200° to 350° C are recorded in Table I as follows:

Table I

Percent Residues of Poly(3,5-dithio-1,2,4-thiadiazole) and Poly[2,5 dithio-1,3,4-thiadiazole][2] At Various Temperatures[1]

| Temperature,C | 200 | 220 | 240 | 260 | 280 | 300 | 320 | 350 |
|---|---|---|---|---|---|---|---|---|
| Poly(3,5-dithio-1,2,4-thiadiazole), Wt. % remained | Initial Wt. loss | 98 | 93 | 92 | 83 | 72 | 33 | 32 |
| Poly(2,5-dithio-1,3,4-thiadiazole) Wt. % remained | Initial Wt. loss | 98 | 28 | 27 | 26 | 25 | 24 | 23 |

[1]Heating rate = 5° C/min. Air Flow rate = 200 cc/min.
[2]See Example 4 for Preparation Furthermore, when a compound, i.e., 3,5-bis(-dodecyldithio)-1,2,4-thiadiazole, (Example 5) subject of the above cited U.S. Pat. No. 3,904,537 was tested in an aluminum-complex grease, its Shell Four-Ball weld point was significantly lower than that of poly(3,5-dithio-1,2,4-thiadiazole) (PDTD). Also the wear prevention characteristics of 3,5-bis(dodecyldithio)-1,2,4-thiadiazole (scar diameter of 0.96 mm) were inferior to that of PDTD (scar diameter of 0.65 mm) and in fact were worse than the blank (scar diameter of 0.82 mm) in a lithium grease tested in the extreme pressure Shell Four-Ball Wear tester (ASTM/D2266).

These observations and the detailed evaluation data listed in Tables II-VII show the unexpected advantages gained by the use as EP agents of the 1,2,4-thiadiazole-based polymers when compared with the non-polymeric 1,2,4-thiadiazole disfulides or with the homopolymer of the isomeric 1,3,4-thiadiazole-3,5-dithiol.

Evaluation of the Polymers of the Present Invention Shell Four-Ball Extreme Pressure Test The Shell Four-Ball EP Test was selected for this study; this machine is probably the most widely used apparatus for this type of work and results can be readily related to the results of other workers in this field. The Shell Four-Ball EP machine consists essentially of a chuck holding a ½-inch diameter steel ball and a cup holding three similar balls in contact. The chuck holding the one ball is rotated at constant speed for a period of 60 seconds, producing a wear scar on the three immobile balls, a constant load on the balls being applied by means of pivoted lever. At the end of the 60-second run the balls are removed and the mean wear scar diameter measured by means of a calibrated microscope Initially, small increases in load produce small increases in the mean wear scar diameter; a point is reached, however, when a small increase in load produces a large increase in the mean wear scar diameter; this load is called the initial seizure load. Beyond this point, small increases in load again produce relatively small increases in the mean wear scar diameter until welding of the balls occur; this load is called the weld point. By obtaining 10 wear scar diameters under 10 different loads below the weld point, one can calculate the Load-Wear Index (Mean-Hertz Load Index) which is a measure of the ability of a lubricant at applied loads (I. P. Standards for Petroleum and Its Products, Method 239/73T).

SELECTION OF THE BASE GREASES

Four base greases, which represent a broad spectrum of the industrial greases used today, were selected to evaluate these new polymers:

1. A lithium grease (mineral oil thickened with lithium stearate; Keystone RM81 light).
2. A clay grease (mineral oil thickened with clay; Keystone RM53).
3. A silicone grease (silicone oil thickened with lithium stearate; Keystone RM89).
4. An aluminum complex grease (mineral oil thickened with aluminum complex; Keystone Zeniplex-2).

All of the base greases are products of the Keystone Division of Pennwalt Corporation.

Liquid lubricants that are used in the lubricating composition of the present invention are mineral oil, water, and synthetic fluids such as silicone fluid. It should be noted that other additives normally found in lubricating compositions can be included in the present lubricating composition such as antioxidants, corrosion inhibitors, detergents suspension agents, viscosity index improvers, etc.

This invention will be more clearly understood by the following specific examples. Unless otherwise stated parts (or percent) are by weight.

EXAMPLE 1

Poly(3,5-dithio-1,2,4-thiadiazole) (PDTD)

a. Dipotassium Cyanodithioimidocarbonate

The salt was prepared according to the procedure of Thaler and McDivitt, J. Org. Chem. 36, 14 (1971) and is incorporated herein by reference.

b. Dipotassium 1,2,4-thiadiazole-3,5-dithiolate

The dithiolate compound was prepared according to the procedure of Thaler and McDivitt, J. Org. Chem. 36, 14 (1971); and is incorporated herein by reference.

c. Poly(3,5-dithio-1,2,4-thiadiazole)

To a solution of 226 g (1.0 mole) of dipotassium 1,2,4-thiadiazole-3,5-ditholate in one liter of water was added a solution of 250.8 g (1.1 moles) of ammonium persulfate in 250 ml of water at 21°-24° C. over a period of 45 minutes during which time solids formed. The mixture was stirred an additional one hour at ambient temperatures and then was filtered. After the solids were washed with 4× 500 ml of water, they were transferred to a Waring Blendor and acidified with dilute hydrochloric acid to pH of 2. The mixture was filtered and after washing with 6 × 500 ml of water, the filter cake was dried in a vacuum desiccator over sodium hydroxide. Yield: 127 g of the desired yellow product, m.p. >300°. Calcd. for $C_2N_2S_3$: C, 16.2; N, 18.9; S, 64.8, elemental S,0.0; Found: C, 16.3; N, 18.5; S, 63.7; elemental S,0.03; mol. wt. >2000.

EXAMPLE 2

Poly{3-[(3 or 4-thiocyclohexyl)ethyldithio] - 5-thio(1,2,4-thiadiazole)} (PTCETD)

To a solution of 141.8 g (0.8 mole) of 3- or 4-(-β-mercaptoethyl)cyclohexanethiol in 600 ml of carbon tetrachloride was added 113.6 g (1.6 moles) of chlorine over a perod of 75 min at a temperature of −5° to −10° C. the solution was purged with nitrogen to remove the hydrogen chloride.

The above cold sulfenyl chloride solution was then added at −7° to −10° C. in 30 min to a solution of 180.8 g (0.8 mole) of dipotassium 1,2,4-thiadiazole-3,5-dithiolate in 450 ml of dimethylformamide. After stirring an additional 30min at −10° C. and then 1 hour at ambient temperatures, the mixture was added to four liters of water. After stirring for 10 minutes, the resulting mixture was filtered. The filter cake, after transferring to a Waring Blendor and washing with water, was dried at 80° C./1 mm Hg to give a quantitative yield of the desired yellow product, softening at 155° C. (semi-solid at 210° C.).

EXAMPLE 3

Poly(3-[(4-methyl-3-thiocyclohecyl)-1-methylethyldithio]-5-thio[1,2,4-thiadiazole]

When 5-(2-mercapto-1-methylethyl)-2-methylcyclohexanethiol is used instead of 3- or 4-(β-mercaptoethyl)cyclohexanethiol in Example 2, the EP-agent obtained is poly(3-[(4-methyl-3-thiocyclohexyl)-1-methylethyldithio]-5-thio(1,2,4-thiadiazole).

EXAMPLE 4

Poly(2,5-dithio-1,3,4-thiadiazole)

To a solution of 194 g (1.0 mole) of disodium (1,3,4-thiadiazole-2,5-dithiolate [prepared according to the procedure of U. Busch, Ber. 27, 2518 (1894)] in one liter of water was added a solution of 251 g (1.1 moles) of ammonium persulfate in 250 ml of water at 21°-24° C. over a period of 45 minutes during which time solids formed. The mixture was stirred an additional one hour at ambient temperatures and then was filtered. After the solids were washed with 4× 500 ml of water, they were transferred to a Waring Blendor and acidified with dilute hydrochloric acid to pH of 2. The mixture was filtered and after washing with 6 × 500 ml of water, the filter cake was dried in a vacuum desiccator over sodium hydroxide. A 94% conversion of yellow solids was obtained having a melting· point of 177°-184° C.

Calcd. for $(C_2N_2S_3)$: C, 16.2; H,0.0; N, 18.5. Found: C, 16.0; H, 0.15; and N, 19.3.

EXAMPLE 5

3,5-Bis(dodecyldithio)-1,2,4,-thiadiazole

To 202.4 g. (1.0 mole) of n-dodecyl mercaptan in 350 ml of carbon tetrachloride was added 71.0 g. (1.0 mole) of chlorine at a temperature of −10° C over a period of 40 minutes. After stirring an additional 10 minutes, the clear orange solution was purged of hydrogen chloride with nitrogen for 15 minutes.

The above solution was then added in 45 minutes to a stirred mixture, at −25° C, of 113 g.(0.5 mole) of dipotassium 1,2,4-thiadiazole-3,5-dithiolate and 750 ml of tetrahydrofuran. The resulting mixture, after stirring at −25° C for an additional one hour and at ambient temperatures for an additional 2 hours, was flash-evaporated to give a turbid oil. Ethyl ether(500 ml) was added; the resulting mixture was filtered; and the filtrate was chilled to −20° C to yield, after filtering and drying, 161 g. (59% conversion) of white solid product, m.p. 31°-32° C.

Calc'd for $C_{26}H_5N_2S_5$: C, 56.7; H, 9.07; N, 5.34; S, 28.8. Found: C, 56.7; H, 9.15; N, 5.09; S, 29.1.

EXAMPLE 6

Extreme Pressure and Antiwear Characteristics of PDTD in Lithium Grease

The weld point of the lithium grease (Keystone KM81) containing 5% PDTD is 560 kg which is considerably higher than those blends containing 10% $MoS_2$, 5% molybdenum oxysulfide dithiocarbamate, 5% antimony dialkyl dithiocarbamate, and 5% phosphorus-sulfur compounds. All of these are commercial additives that are commonly used to improve extreme pressure and antiwar properties of lubricants. The wear reductions observed at higher loads for samples containing 5% PDTD were significant as indicated by the small wear scar diameter at 530 kg (1.97 mm) just before the weld point vs 2.26 mm at 250 kg for 10% $MoS_2$ and 3.08 mm at 266 kg for 5% molybdenum oxysulfide dithiocarbamate. The results are recorded in Table II.

The load-wear indices and initial seizure loads of the lithium grease and its blends containing 10% $MoS_2$, 5% molybdenum oxysulfide dithiocarbamate and 5% PDTD were obtained and the results are recorded in Table III. The higher the value of load-wear index of a lubricant the greater is its ability to prevent wear with increased loads and the greater is its load-carrying capacity. The load-wear index of the 5% PDTD blend is 84 vs 39 and 43 for the 5% molybdenum oxysulfide dithiocarbamate and 10% $MoS_2$ blend, respectively. The initial seizure load of the 5% PDTD blend is higher than the 5% molybdenum oxysulfide dithiocarbamate, but slightly lower than the 10% $MoS_2$ blend.

EXAMPLE 7

Extreme Pressure and Antiwear Characteristics of PDTD in Silicone Grease

The Shell Four-Ball extreme pressure and antiwear characteristics of the silicone grease (keystone RM89) and its blends are recorded in Table IV. The weld point of the 5% PDTD blend is 400 kg vs 160 kg for the base grease, 224 kg for the 5% molybdenum oxysulfide dithiocarbamate blend and 266 kg for the 5% antimony dialkyldithiocarbamate blend. Significant wear reduction at high loads was observed on the 5% PDTD blend in comparison with other blends as indicated by the wear scar diameters just before the weld points.

Table II

Shell Four-Ball Extreme Pressure and Antiwear Characteristics

| Grease Composition | Extreme Pressure and Antiwear Properties[1] (ASTM D2596) | |
|---|---|---|
| | Weld Point, kg | Scar Diameter before Weld, mm (kg) |
| Lithium Grease (base)[2] | 140 | — |
| Lithium Grease+5% MoS$_2$ | 170 | — |
| Lithium Grease+10% MoS$_2$ | 266 | 2.26(250) |
| Lithium Grease+5% molybdenum oxysulfide dithiocarbamate | 280 | 3.08(266) |
| Lithium Grease+5% antimony dialkyldithiocarbamate | 250 | 3.08(236) |
| Lithium Grease+5% sulfur-phosphorus package | 200 | 2.57(190) |
| Lithium Grease+5% PDTD | 560 | 1.97(530) |

[1] AISI 52100 steel on steel.
[2] Lithium Grease (mineral oil thickened with lithium stearate; Keystone RM 81 light, Keystone Division, Pennwalt Corporation).

Table III

Wear-Load Indices and Initial Seizures Loads of Lithium Grease and Its Blends Containing Various Additives

| Grease Composition | Initial Seizure Load, kg | Load-Wear Index |
|---|---|---|
| Lithium Grease* | 52 | 18 |
| Lithium Grease + 5% molybdenum oxysulfide dithiocarbamate | 100 | 39 |
| Lithium Grease + 10% MoS$_2$ | 120 | 43 |
| Lithium Grease + 5% PDTD | 110 | 84 |

*Lithium grease - mineral oil thickened with lithium stearate (Keystone RM 81 light, Keystone Division, Pennwalt Corporation).

Table IV

Shell Four-Ball Extreme Pressure and Antiwear Characteristics of Silicone Grease and Its Blends Containing Various Additives

| Grease Composition | Extreme Pressure and Antiwear Properties[1] (ASTM D2596) | |
|---|---|---|
| | Weld Point, kg | Scar Diameter before Weld, mm (kg) |
| Silicone grease [2] | 160 | — |
| Silicone grease + 5% molybdenum oxysulfide dithiocarbamate | 224 | 3.33 (210) |
| Silicone grease + 5% antimony dialkyl dithiocarbamate | 266 | 3.62 (250) |
| Silicone grease + 5% PDTD | 400 | 2.63 (378) |

[1] AISI 52100 steel on steel.
[2] Silicone grease - silicone fluid thickened with lithium stearate (Keystone RM89, Keystone Division, Pennwalt Corporation).

EXAMPLE 8

Extreme Pressure and Antiwear Characteristics of PDTD in Clay Grease

The Shell Four-Ball EP and antiwear properties of the clay grease (Keystone 53) and its blends containing 5% molybdenum oxysulfide dithiocarbamate and 5% PDTD are recorded in Table V. Again the weld point of the 5% PDTD blend is higher than for the other blends and the base grease.

EXAMPLE 9

Extreme Pressure and Antiwear Characteristics of PDTD in Aluminum Complex Grease The weld points of the aluminum complex grease and its blends containing 5% PDTD and 5% molybdenum oxysulfide dithiocarbamate are listed in Table VI. The weld point of the 5% PDTD is significantly higher than those of the base grease and the 5% molybdenum oxysulfide dithiocarbamate blend. The antiwear characteristics of the 5% PDTD blend are much superior to the other formulations as indicated by its lower scar diameter just before welding.

EXAMPLE 10

Extreme Pressure and Antiwear Characteristics of PTCETD) in Lithium Grease

The weld point of 5% PTCETD in lithium grease is 378 Kg which is significantly higher than other commerical additives investigated in the same base grease. The antiwear characteristics at higher loads of the 5% PTECTD blend is superior as indicated by its relatively small scar diameter before welding. The results are listed in Table VII.

EXAMPLE 11

The weld point of a paste prepared by suspending 5% PDTD in a mineral oil (solvent refined bright stock; 158 SUS at 210° F) was found to be 560 Kg which is significantly higher than the base fluid (weld point, 140 Kg).

EXAMPLE 12

The weld point of a silicone suspension (5% PDTD in methylphenyl polysiloxane) showed 60% improvement over the blank, i.e. base fluid alone.

Table V

Shell Four-Ball Extreme Pressure and Antiwear Characteristics of Clay Grease and Its Blends Containing Various Additives

| Grease Composition | Extreme Pressure and Antiwear Properties[1] (ASTM D2596) | |
|---|---|---|
| | Weld Point, kg | Scar Diameter before Weld, mm (kg) |
| Clay grease [2] | 200 | — |
| Clay grease + 5% molybdenum oxysulfide dithiocarbamate | 266 | 2.91 (250) |
| Clay grease + 5% PDTD | 378 | 3.78 (355) |

[1] AISI 52100 steel on steel.
[2] Clay grease - mineral oil thickened with clay (Keystone RM 53, Keystone Division, Pennwalt Corporation).

Table VI

Shell Four-Ball Extreme Pressure and Antiwear Characteristics of an Aluminum Complex Grease And Its Blends Containing Various Additives

| Grease Composition | Extreme Pressure and Antiwear Properties[1] (ASTM D2596) | |
|---|---|---|
| | Weld Point, kg | Scar Diameter before Weld, mm (kg) |
| Aluminum complex grease[2] | 126 | — |
| Aluminum complex grease + 5% molybdenum oxysulfide dithiocarbamate | 200 | 2.46 (190) |
| Aluminum complex grease + 5% PDTD | 355 | 2.05 (315) |

[1] AISI 52100 steel on steel.
[2] Aluminum complex grease - mineral oil thickened with aluminum complex (Keystone Zeniplex-2, Keystone Division Pennwalt Corporation).

Table VII

Extreme Pressure and Antiwear Characteristics of Lithium Grease and Its Blends Containing Various Additives

| Grease Composition | Weld Point, kg | Scar Diameter before Weld, mm (kg) |
|---|---|---|
| Lithium grease[2] | 140 | — |
| Lithium grease + 10% MoS$_2$ | 266 | — |
| Lithium grease + 5% molybdenum oxysulfide dithiocarbamate | 280 | 3.08 (266) |
| Lithium grease + 5% antimony dialkyl dithiocarbamate | 250 | 3.08 (236) |
| Lithium grease + 5% PTECTD | 378 | 2.56 (355) |

[1] AISI 52100 steel on steel.
[2] Lithium grease - mineral oil thickened with lithium stearate (Keystone RM 81 light, Keystone Division, Pennwalt Corporation).

We claim:

1. A composition having the formula

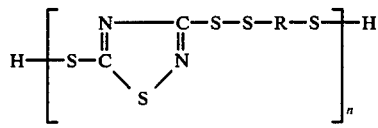

wherein
R is selected from the group consisting of

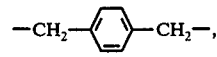

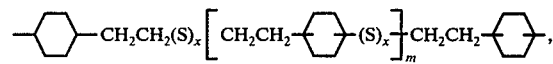

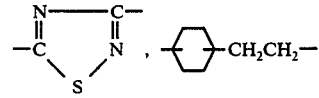

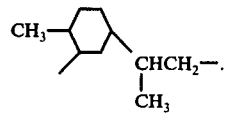

phenylene, an alkylene or substitute alkylene of 2-50 carbons. cyclic alkylene or substituted cyclic alkylene of 5-50 carbons wherein the alkylene or cyclic alkylene can contain oxygen and/or sulfur atoms, or $(S)_x$ groups;

$m$ is an integer of 0–10;
$n$ is an integer of 5–100;
$x$ is an integer of 1–5.

2. The composition of claim 1 wherein is

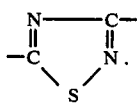

3. The composition of claim 1 wherein R is

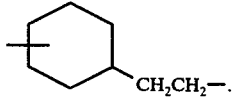

4. A lubricating composition comprising a major amount of a lubricating grease or liquid and a minor amount of the composition of claim 1.

5. The composition of claim 4 wherein the major amount of the lubricating grease is 80–99.9 parts of a grease selected from the group consisting of lithium grease, silicone grease, clay grease, and aluminum complex grease and the minor amount of the composition of is 0.1–20 parts.

6. The lubricating composition of claim 4 wherein the liquid lubricant is selected from mineral oil, water, and synthetic fluids.

7. A lubricating composition comprising a major amount of a mineral oil and 0.1–20 parts of the composition of claim 2.

8. A lubricating composition comprising a major amount of a silicone fluid and parts of the composition of claim 2.

* * * * *

UNITED STATES PATENT OFFICE
CERTIFICATE OF CORRECTION

Patent No. 4,107,059                Dated August 15, 1978

Inventor(s) James Ping King, Everett A. Mailey, Ivan Christoff Popoff

It is certified that error appears in the above-identified patent and that said Letters Patent are hereby corrected as shown below:

In line 46, column 10, it reads:

"amount of a silicone fluid and parts of the composition"

It should read:

--amount of a silicone fluid and 0.1-20 parts of the composition--

On line 16, column 10, it reads:

"2. The composition of claim 1 wherein is"

It should read:

Signed and Sealed this

Nineteenth Day of June 1979

[SEAL]

Attest:

RUTH C. MASON
Attesting Officer

DONALD W. BANNER
Commissioner of Patents and Trademarks